US007650175B2

(12) United States Patent
Liao et al.

(10) Patent No.: US 7,650,175 B2
(45) Date of Patent: Jan. 19, 2010

(54) METHOD AND DEVICE FOR DETECTING FAULT IN A BLOOD OXYGEN SENSOR

(75) Inventors: Zhongshu Liao, Shenzhen (CN); Jilun Ye, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 685 days.

(21) Appl. No.: 11/316,189

(22) Filed: Dec. 22, 2005

(65) Prior Publication Data

US 2006/0206020 A1 Sep. 14, 2006

(30) Foreign Application Priority Data

Mar. 10, 2005 (CN) .................. 2005 1 0033595

(51) Int. Cl.
*A61B 5/1455* (2006.01)
*G01L 25/00* (2006.01)
(52) U.S. Cl. .................... 600/323; 600/310; 250/252.1
(58) Field of Classification Search ......... 600/309–344; 250/252.1
See application file for complete search history.

(56) References Cited

U.S. PATENT DOCUMENTS

| 4,928,692 | A | * | 5/1990 | Goodman et al. | ............ 600/324 |
| 5,783,821 | A | * | 7/1998 | Costello, Jr. | ............. 250/252.1 |
| 6,297,661 | B1 | | 10/2001 | Chen | |
| 6,356,774 | B1 | * | 3/2002 | Bernstein et al. | ............ 600/323 |

FOREIGN PATENT DOCUMENTS

CN 1475811 2/2004
JP A-2002-35950 2/2002
JP A-2004-117260 4/2004

OTHER PUBLICATIONS

Search Report from Chinese Patent Application No. 200510033595.1.
English Translation of the non-English language documents.
Search Report from Chinese Patent Application No. 200510033595.1.

* cited by examiner

*Primary Examiner*—Eric F Winakur
(74) *Attorney, Agent, or Firm*—Kory D. Christensen; Stoel Rives LLP

(57) ABSTRACT

A device for measuring blood oxygen content comprises a blood oxygen sensor interface, a signal processing unit, and a plurality of voltage sampling points. A method for detecting fault in a blood oxygen sensor comprises the steps of: connecting the blood oxygen sensor to the signal processing unit; providing voltage signals by the signal processing unit via a pair of testing terminals, for alternately driving two LEDs connected in inverse-parallel with each other in the blood oxygen sensor; sampling the voltages of the pair of testing terminals, respectively, and determining the fault relevant to the LEDs based on the relationship of the voltages; receiving current signals from a photodiode in the blood oxygen sensor by the signal processing unit via another pair of terminals, converting the received current signals into voltage signals, and outputting positive voltage signals via a reverser and a follower, respectively; and sampling the positive voltage signals respectively for determining the fault relevant to the photodiode. Thus, the fault of the sensor can be detected and determined by employing a plurality of sampling points without the tissue to be measured of the human body, thereby the output error due to the faults of the sensor can be avoided, and the device can be maintained conveniently.

11 Claims, 2 Drawing Sheets ered in the process of medical operation and recovery.
METHOD AND DEVICE FOR DETECTING FAULT IN A BLOOD OXYGEN SENSOR This application claims the benefit of Chinese Patent Application No. 200510033595.1, filed Mar. 10, 2005, the contents of which are incorporated herein by reference in their entirety.

FIELD OF THE INVENTION

The present invention relates to a medical instrument, in particular a device for measuring blood oxygen saturation, and especially to a method for detecting fault in a blood oxygen sensor.

BACKGROUND OF THE INVENTION

It is very necessary to monitor the state of blood oxygen for patients in the process of medical operation and recovery. Generally, this is performed by monitoring the blood oxygen saturation (namely the oxygen content of arterial blood). In a human body, the arterial blood pulsates in the ends of tissues as a result of the pulse wave, and the oxyhemoglobin ($HbO_2$) and the reduced hemoglobin (Hb) cause the media to be measured (such as fingers or toes, etc.) to have different transmittivities of red light and infrared light. Nowadays, domestic or foreign pulse oximeters operate by utilizing the above principle, that is: irradiating red light and infrared light of a certain intensity to the media to be measured, detecting the transmitted light intensities of the two lights, and then calculating the blood oxygen saturation based on the ratio of the density variations of the red light and the infrared light after the two lights passing through the media to be measured such as fingers.

Based on the measuring principle described above, a device for non-traumatic measurement of blood oxygen saturation basically comprises a blood oxygen sensor and a signal processing unit. The key component of the blood oxygen sensor is a sensor including a light-emitting diode (LED) and a photosensor. At one side of the sensor, the LED can provide lights of two or more wavelengths; and at the other side of the sensor, the photosensor can convert the light signals passing through the measured media between the LED and the photosensor and containing the information of blood oxygen saturation into electrical signals which are transmitted to the signal processing unit to be digitized for calculating the blood oxygen saturation.

FIG. 1 shows the main structure of the blood oxygen sensor. As shown in FIG. 1, a blood oxygen sensor 1 comprises a sensor head 11, a signal transmission cable 12 and a connector 13. The sensor head 11 comprises a photodiode 111, a first LED 114 (emitting red lights) and a second LED 115 (emitting infrared lights), the first LED 114 and the second LED 115 being connected in inverse-parallel with each other. The signal transmission cable 12 comprises an external shielding layer 126, an internal shielding layer 121, a first core 122 and a second core 123, the first core 122 and the second core 123 being connected to a cathode pin 112 and an anode pin 113 of the photodiode 111, respectively, for transmitting the current modulated by the photodiode 111. Moreover, the first core 122 and the second core 123 are enwrapped by the internal shielding layer 121. The signal transmission cable 12 further comprises a third core 124 and a fourth core 125 in parallel with the internal shielding layer 121, the third core 124 and the fourth core 125 being connected to both pins of the first LED 114, respectively, for transmitting the current which alternately drives the first LED 114 and the second LED 115.

The sensor head 11 is connected to a signal processing unit 2 (for example, a blood oxygen module circuit) via the signal transmission cable 12 and the connector 13 in turn. Thus, the lights transmitting through the tissue can be received by the blood oxygen sensor and converted into electrical signals, and then supplied to subsequent devices for further processing.

The normal operation of the oximeter for measuring the blood oxygen saturation is based on the reliable and fault-free blood oxygen sensor. As the sensor head 11, the signal transmission cable 12 and the connector 13 are movable components, they tend to be damaged in use. For example, the first core 122 and the second core 123 may be in short-circuit connection with the internal shielding layer 121, or the third core 124 may be in short-circuit connection with the fourth core 125, or the first LED 114 or the second LED 115 may be short-circuited. All these faults will cause the oximeter to operate abnormally and output incorrect data. Therefore, it is necessary to monitor the fault of the blood oxygen sensor 1 and output prompt messages in the signal processing unit 2.

Generally, the intensities of the current signals coming from the blood oxygen sensor vary depending on the intensities of the pulse wave signals of the human body. But if any of the above-mentioned faults occurs in the sensor, the photodiode cannot output the light-modulated current signals whose intensities vary depending on the intensities of the pulse wave signals of the human body. The signal processing unit 2 existing in prior arts can judge whether or not any fault occurs in the sensor on the basis of the above feature.

However, there are the following limitations and disadvantages in the prior arts described above. Only when the measured part of the human body is positioned in the sensing range of the sensor can the signal processing unit judge whether or not any fault occurs in the sensor on the basis of the characteristic of the pulse wave of the human body. Furthermore, if the photodiode outputs a signal whose characteristic is similar to that of the pulse wave as a result of other factors such as ambient lights, a wrong determination will be made by adopting the above-mentioned method. Thus, it's not sure whether the fault can be found in time once the fault occurs in the blood oxygen sensor, and this will affect the monitoring of the blood oxygen of patients.

SUMMARY OF THE INVENTION

In view of the limitations and disadvantages in the prior arts, an object of the present invention is to provide a method and device for detecting fault in a blood oxygen sensor. According to the method and device in the present invention, the faults of the sensor can be accurately detected in time without the part to be measured of the human body, and the type of the faults can be immediately determined. Thus, it's convenient for the device for measuring blood oxygen content to output corresponding messages of the faults or perform corresponding treatments in time on the basis of the type of the faults, and the reliability and accuracy of the measurement can be improved effectively.

In order to achieve the object described above, the general concept of the present invention is proposed as follows. Based on the characteristic of positive voltage drop of two LEDs working in normal operation status, the two LEDs are alternately driven by a signal processing unit, and the voltages to ground of two connecting points in the signal processing unit are detected, wherein the two connecting points serve to connect the cathodes and anodes of the LEDs respectively, thereby the faults relevant to the LEDs that occur in the blood oxygen sensor can be determined; the two LEDs are alternately driven by the signal processing unit; based on the loop current in the photodiode, the current is converted into two voltages to ground at two interface terminals by the signal processing unit, and the two voltages to ground are detected respectively, thereby the faults relevant to the LEDs that occur in the blood oxygen sensor can be determined.

According to one aspect of the present invention, there is provided a method for detecting fault in a blood oxygen sensor, which is used in a device for measuring blood oxygen content, comprising the steps of:

a. making sure that the blood oxygen sensor has been connected to the signal processing unit, and then powering on the device for measuring blood oxygen content to the operating status;

b. alternately outputting, from the signal processing unit, voltage signals of reverse polarities via a pair of testing terminals, for alternately driving the two LEDs connected in inverse-parallel with each other in the blood oxygen sensor;

c. sampling voltages to ground of the pair of testing terminals respectively and generating a group of comparison voltages V3 and V4 by the device for measuring blood oxygen content each time the signal processing unit outputs a voltage signal of one polarity; and d. determining the faults relevant to the LEDs that occur in the blood oxygen sensor on the basis of the comparison voltages V3 and V4 by the device for measuring blood oxygen content.

In the method described above, if it is determined in the step d that no fault relevant to the LEDs occurs in the blood oxygen sensor, the method further comprises the steps of:

e. receiving current signals from the photodiode in the blood oxygen sensor by the signal processing unit via another pair of terminals; converting the current signals flowing through the pair of terminals into voltage signals via two current-voltage converters which are connected to one of the pair of terminals, respectively; then outputting positive voltage signals via a reverser and a follower, respectively;

f. sampling the positive voltage signals output from the reverser and the follower, respectively, and generating another group of comparison voltages V1 and V2 by the device for measuring blood oxygen content; and g. determining the faults relevant to the photodiode that occur in the blood oxygen sensor on the basis of the comparison voltages V1 and V2 by the device for measuring blood oxygen content.

According to another aspect of the present invention, there is provided a device for measuring blood oxygen content used for detecting fault in a blood oxygen sensor, the device comprising a signal processing unit and a blood oxygen sensor interface, in which the blood oxygen sensor interface serves to provide input and output signals for connecting the signal processing unit to the blood oxygen sensor, and comprises a pair of input and output ports for providing the driving voltages to operate LEDs in the blood oxygen sensor, a pair of input and output ports for receiving currents from a photodiode in the blood oxygen sensor, and a ground terminal for making shielding layers in the blood oxygen sensor common ground with the signal processing unit; particularly, the signal processing unit comprises a polarity exchange device for exchanging the polarities of the driving voltages, and the signal processing unit further comprises at least two voltage sampling points, the voltages of which are detected to determine the faults relevant to the blood oxygen sensor.

In the device described above, the two voltage sampling points are provided at the pair of input and output ports in the blood oxygen sensor interface for providing the driving voltages to operate the LEDs in the blood oxygen sensor; the signal processing unit further comprises a reverser and a follower each connected to an output port of a corresponding one of two current-voltage converting circuits; the input ports of the two current-voltage converting circuits are connected to the input and output ports in the blood oxygen sensor interface for receiving currents from the photodiode in the blood oxygen sensor, respectively; and each of the output terminals of the reverser and the follower comprises a voltage sampling point, respectively.

According to the method and device described above, whether or not a fault occurs in the sensor operating in the device can be determined, without the part to be measured of the human body, by directly detecting the voltage parameters of a plurality of key points in the signal processing unit, and the positions and types of the faults can be accurately determined. Thus, the device for measuring blood oxygen content can perform corresponding treatments based on the type of the faults, the output error due to the faults of the sensor can be avoided effectively, and the device can be maintained conveniently.

DESCRIPTION OF THE PREFERRED EMBODIMENTS

Now the present invention will be further described in connection with the preferred embodiments with reference to the drawings.

Figure 1:
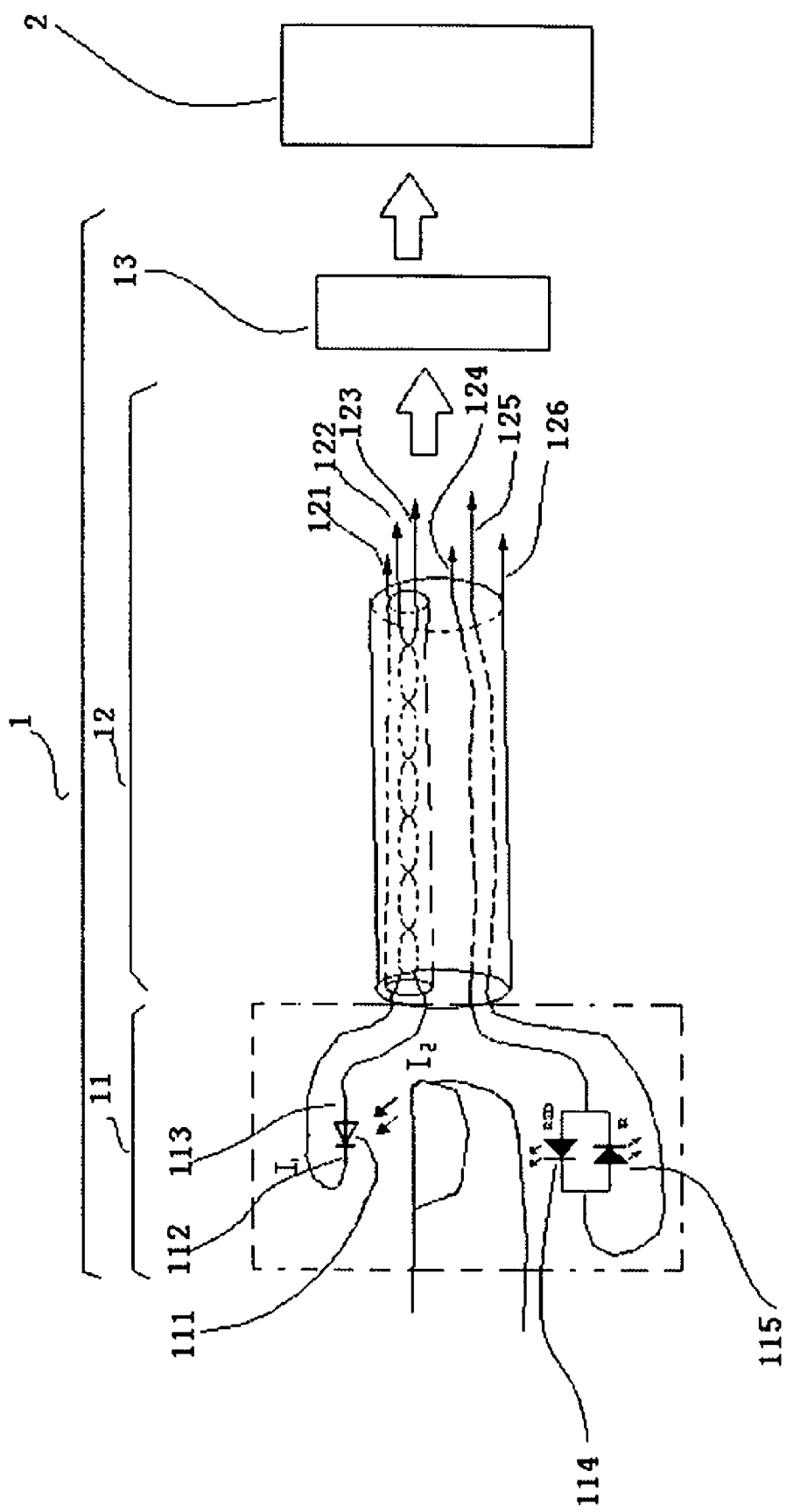
FIG. 1 is a schematic diagram showing the main structure of a blood oxygen sensor.
Figure 2:
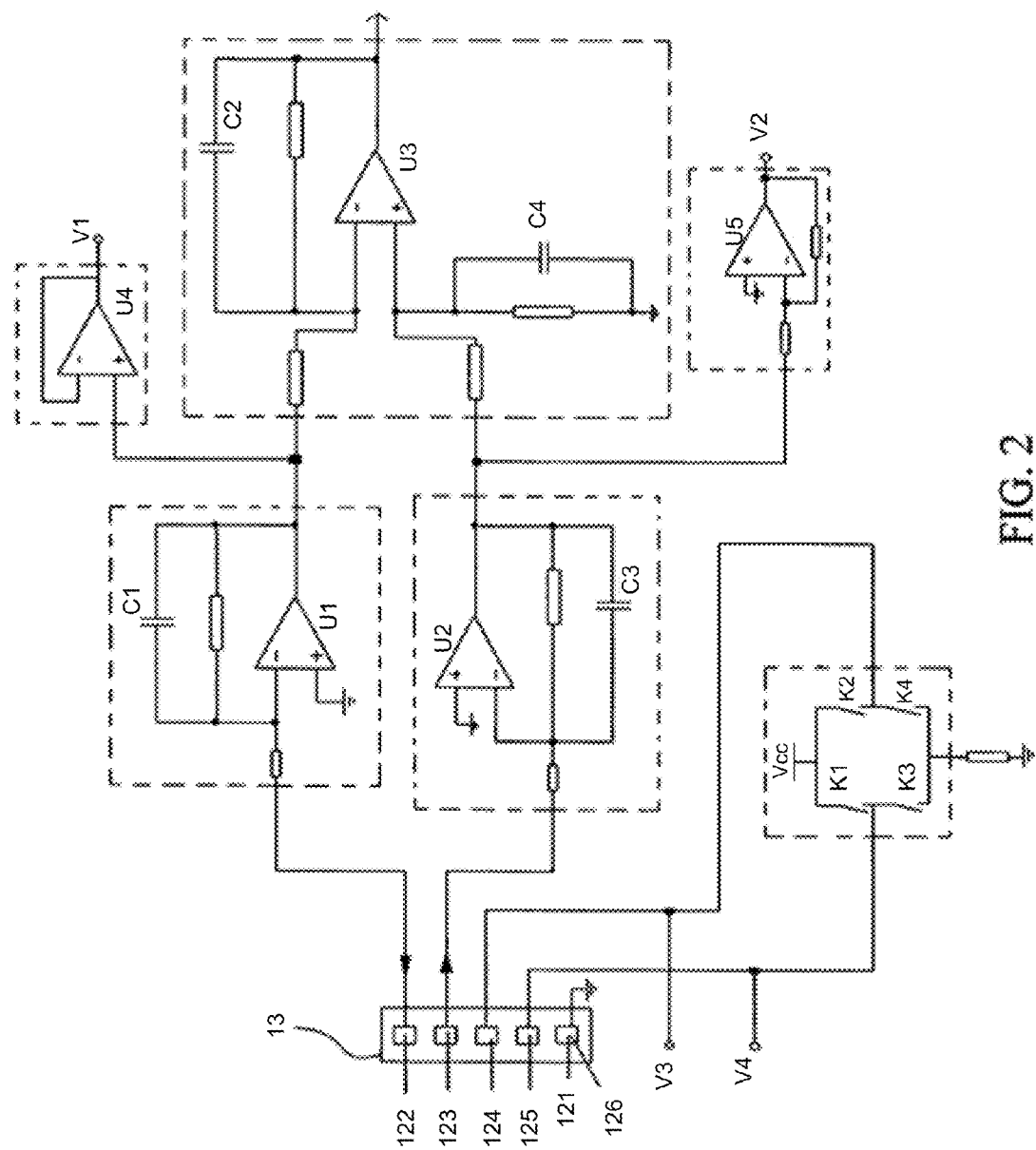
FIG. 2 is a block diagram showing the fault detecting circuit in a signal processing unit according to the present invention.

As shown in FIG. 2, a device for measuring blood oxygen content according to present embodiment comprises a blood oxygen sensor interface and a signal processing unit 2. The blood oxygen sensor interface serves to provide input and output signals for connecting the signal processing unit 2 with a blood oxygen sensor, and comprises a pair of input and output ports for providing the driving voltages to operate the LEDs in the blood oxygen sensor. The pair of input and output ports are connected to the two terminals of a first LED 114 and a second LED 115 connected in inverse-parallel with each other in a sensor head 11 via a third core 124 and a fourth core 125 in a signal transmission cable 12, respectively (as shown in FIG. 1). The signal processing unit 2 provides power supplies of reverse polarities for the input and output ports by switching between a power supply and a ground-resistance via four switch units K1, K2, K3 and K4, so as to alternately drive the first LED 114 and the second LED 115 to emit lights. During a normal operation, when the signal processing unit 2 applies VCC to the fourth core 125 by switching on K1 and K4 and switching off K2 and K3, the voltage on the third core 124 is (VCC−$V_{IR}$), where $V_{IR}$ is the positive voltage drop on the second LED 115; in contrast, when the signal processing unit 2 applies VCC to the third core 124 by switching on K2 and K3 and switching off K1 and K4, the voltage on the fourth core 125 is (VCC−$V_{RED}$), where $V_{RED}$ is the positive voltage drop on the first LED 114. It will be apparent to those skilled in the art that the four switch units K1, K2, K3 and K4 can be replaced by any other exchange device existing in the prior arts for changing the polarity of the driving voltage, the detailed description of which will be omitted herein.

The blood oxygen sensor interface further comprises a ground terminal for making the shielding layers (the external shielding layer 126 and the internal shielding layer 121) in the blood oxygen sensor common ground with the signal processing unit, and a pair of input and output ports for receiving the current modulated by a photodiode in the blood oxygen sensor. The pair of input and output ports are connected to two pins of the photodiode 111 via a first core 122 and a second core 123 in the signal transmission cable 12, respectively. During a normal operation, the light emitted from the first LED 114 or the second LED 115 irradiates the photodiode 111 to generate a current flowing in the photodiode 111 only in one direction, thereby "outputting" the currents of equal intensities and reverse directions through the first core 122 and the second core 123, respectively. The currents flowing through the first core 122 and the second core 123 are respectively transmitted to an input port of a corresponding one of two current-voltage converting circuits in which the currents are converted into voltage signals of reverse polarities, and then transmitted at the same time to a signal amplifier 204 for further processing.

Generally, the blood oxygen sensor interface is in the physical form of a connector such as a connector 13 that can adaptively couple with the blood oxygen sensor. In addition, the blood oxygen sensor interface can be in the form of a general connecting line or a distributed line, the detailed descriptions of which will be omitted herein.

In order to achieve the object of the present invention, a plurality of voltage sampling points are provided in the signal processing unit in the device for measuring blood oxygen content according to the present embodiment. The voltages at the voltage sampling points are detected to determine the faults relevant to the blood oxygen sensor. In the blood oxygen sensor interface, one of the voltage sampling points can be provided at the input and output ports for providing the driving voltages to operate the LEDs in the blood oxygen sensor, respectively. One terminal connected to the third core 124 is denoted by V3, and the other terminal connected to the fourth core 125 is denoted by V4. The faults relevant to the LEDs that occur in the blood oxygen sensor can be determined by comparing the voltages of V3 and V4.

In order to determine, without the part to be measured of the human body, the faults relevant to the photodiode that occur in the blood oxygen sensor, another two voltage sampling points are provided in the device for measuring blood oxygen content. The signal processing unit further comprises a reverser and a follower each connected to an output port of a corresponding one of two current-voltage converting circuits for converting the voltage signals of reverse polarities in two ways into positive voltage outputs of same polarity. The input ports of the two current-voltage converting circuits are connected to the input and output ports in the blood oxygen sensor interface for receiving the inductive current from the photodiode in the blood oxygen sensor, respectively. Each of the output terminals of the reverser and the follower comprises a voltage sampling point V2 and V1, respectively. The two current-voltage converting circuits are a pair of circuits with the same configuration parameters. During a normal operation, the following mathematical expression can be satisfied: $V1=V2\neq0$.

Therefore, with respect to the device for measuring blood oxygen content according to the embodiment described above, a method for detecting fault in a blood oxygen sensor comprises the steps of:

a. making sure that the blood oxygen sensor has been connected to the signal processing unit, and then powering on the device for measuring blood oxygen content to the operating status;

b. alternately outputting, from the signal processing unit, voltage signals of reverse polarities via a pair of testing terminals, for alternately driving the two LEDs connected in inverse-parallel with each other in the blood oxygen sensor;

c. sampling voltages to ground of the pair of testing terminals respectively and generating a group of comparison voltages V3 and V4 by the device for measuring blood oxygen content each time the signal processing unit outputs a voltage signal of one polarity; and d. determining the faults relevant to the LEDs that occur in the blood oxygen sensor on the basis of the comparison voltages V3 and V4 by the device for measuring blood oxygen content.

In the step d, the specific method for determining the faults is based on two groups of data of V3 and V4 that are obtained in adjacent two samplings, wherein:

1) if V3 always equals to V4, the third core 124 is in short-circuit connection with the fourth core 125, or the first LED 114 or the second LED 115 is broken through;

2) if V3 always doesn't equal to V4, and neither of V3 and V4 equals to zero, no fault relevant to the LEDs occurs in the blood oxygen sensor;

3) if V3 always equals to zero, the third core 124 is in short-circuit connection with the ground; and 4) if V4 always equals to zero, the fourth core 125 is in short-circuit connection with the ground.

In the method described above, if it is determined that no fault relevant to the LEDs occurs in the blood oxygen sensor, the method further comprises the steps of:

e. receiving current signals from the photodiode in the blood oxygen sensor by the signal processing unit via another pair of terminals; converting the current signals flowing through the pair of terminals into voltage signals via two current-voltage converters which are connected to one of the pair of terminals, respectively; then outputting positive voltage signals via a reverser and a follower, respectively;

f. sampling the positive voltage signals output from the reverser and the follower, respectively, and generating another group of comparison voltages V1 and V2 by the device for measuring blood oxygen content; and g. determining the faults relevant to the photodiode that occur in the blood oxygen sensor on the basis of the comparison voltages V1 and V2 by the device for measuring blood oxygen content.

In the step g, the specific method for determining the faults is based on two groups of data of V1 and V2 that are obtained in adjacent two samplings, wherein:

1) if always V1=V2=0, the photodiode and the signal transmitting lines thereof are in an open-circuit or a short-circuit condition, for example, the first core 122 or the second core 123 is in an open-circuit condition, or the first core 122 is in short-circuit connection with the second core 123;

2) if V1 always doesn't equal to V2, and neither of V1 and V2 equals to zero, the first core 122 or the second core 123 is in short-circuit connection with the third core 124 or the fourth core 125;

3) if either of V1 and V2 always equals to zero and the other of them always doesn't equal to zero, the first core 122 is in short-circuit connection with the ground (the shielding lines) in case of V1 equals to zero, or the second core 123 is in short-circuit connection with the ground (the shielding lines) in case of V2 equals to zero; and 4) if always $V1=V2\neq0$, no fault occurs in the blood oxygen sensor.

Based on the method described above, the device for measuring blood oxygen content according to the present embodiment can, without the part to be measured of the human body, determine whether or not any fault occurs in the blood oxygen sensor as well as the type of the faults by directly detecting four detection-points V1, V2, V3 and V4.

The method described above is proved to be practical in the device for measuring blood oxygen content existing in the prior arts. The operation of the device for measuring blood oxygen content can be interrupted at predetermined timings for detecting the blood oxygen sensor. Moreover, corresponding prompt messages can be displayed according to the type of the faults. Thus, it is convenient for the maintenance of the device, and output errors due to the faults of the sensor can be avoided effectively.

In addition, the amplifiers U1 to U5 shown in FIG. 2 can be integrated operational amplifiers, and the capacitors C1 to C4 can be filter capacitors.

What is claimed is:

1. A method for detecting fault in a blood oxygen sensor, which is used in a device for measuring blood oxygen content, wherein the method comprises the steps of:
   a. connecting the blood oxygen sensor to a signal processing unit;
   b. alternately outputting, from the signal processing unit, voltage signals of reverse polarities via a pair of testing terminals, for alternately driving the two LEDs connected in inverse-parallel with each other in the blood oxygen sensor;
   c. sampling voltages to ground of the pair of testing terminals respectively and generating a group of comparison voltages V3 and V4 by the device for measuring blood oxygen content each time the signal processing unit outputs a voltage signal of one polarity; and
   d. determining the faults relevant to the LEDs that occur in the blood oxygen sensor by comparing the voltages V3 and V4.

2. The method for detecting fault in a blood oxygen sensor according to claim 1, wherein in the step d, the method for determining the faults by comparing V3 and V4 comprises:
   1) if V3 always equals to V4, a third core is in short-circuit connection with a fourth core, or a first LED or a second LED is broken through;
   2) if V3 always doesn't equal to V4, and neither of V3 and V4 equals to zero, no fault relevant to the LEDs occurs in the blood oxygen sensor;
   3) if V3 always equals to zero, the third core is in short-circuit connection with the ground; and
   4) if V4 always equals to zero, the fourth core is in short-circuit connection with the ground.

3. The method for detecting fault in a blood oxygen sensor according to claim 2, wherein if it is determined in step d that no fault relevant to the LEDs occurs in the blood oxygen sensor, the method further comprises the steps of:
   e. receiving current signals from a photodiode in the blood oxygen sensor by the signal processing unit via another pair of terminals; converting the current signals flowing through the pair of terminals into voltage signals via two current-voltage converters which are connected to one of the pair of terminals, respectively; then outputting positive voltage signals via a reverser and a follower, respectively;
   f. sampling the positive voltage signals output from the reverser and the follower, respectively, and generating another group of comparison voltages V1 and V2 by the device for measuring blood oxygen content; and
   g. determining the faults relevant to the photodiode that occur in the blood oxygen sensor on the basis of the comparison voltages V1 and V2 by the device for measuring blood oxygen content.

4. The method for detecting fault in a blood oxygen sensor according to claim 3, wherein in the step g, the method for determining the faults based on two groups of data of V1 and V2 that are obtained in adjacent two samplings is:
   1) if always V1=V2=0, the photodiode and the signal transmitting lines thereof are in an open-circuit or a short-circuit condition, that is, the first core or the second core is in an open-circuit condition, or the first core is in short-circuit connection with the second core;
   2) if V1 always doesn't equal to V2, and neither of V1 and V2 equals to zero, the first core or the second core is in short-circuit connection with the third core or the fourth core;
   3) if either of V1 and V2 always equals to zero and the other of them always doesn't equal to zero, the first core is in short-circuit connection with the ground or the shielding lines in case of V1 equals to zero, or the second core is in short-circuit connection with the ground or the shielding lines in case of V2 equals to zero; and
   4) if always V1=V2≠0, no fault occurs in the blood oxygen sensor.

5. A device for measuring blood oxygen content used for detecting fault in a blood oxygen sensor, the device comprising a signal processing unit and a blood oxygen sensor interface, in which the blood oxygen sensor interface serves to provide input and output signals for connecting the signal processing unit to the blood oxygen sensor, and comprises a pair of input and output ports for providing the driving voltages to operate LEDs in the blood oxygen sensor, a pair of input and output ports for receiving currents from a photodiode in the blood oxygen sensor, and a ground terminal for making shielding layers in the blood oxygen sensor common ground with the signal processing unit; wherein
   the signal processing unit comprises a polarity exchange device for exchanging the polarities of the driving voltages, and at least two voltage sampling points, and wherein
   the signal processing unit is configured to compare the voltages to one another to determine faults relevant to the blood oxygen sensor.

6. The device for measuring blood oxygen content used for detecting fault in a blood oxygen sensor according to claim 5, wherein the two voltage sampling points are provided at the pair of input and output ports in the blood oxygen sensor interface for providing the driving voltages to operate the LEDs in the blood oxygen sensor.

7. The device for measuring blood oxygen content used for detecting fault in a blood oxygen sensor according to claim 5, wherein
   the signal processing unit further comprises a reverser and a follower each connected to an output port of a corresponding one of two current-voltage converting circuits;
   the input ports of the two current-voltage converting circuits are connected to the input and output ports in the blood oxygen sensor interface for receiving currents from the photodiode in the blood oxygen sensor, respectively; and
   each of the output terminals of the reverser and the follower comprises a voltage sampling point, respectively.

8. The device for measuring blood oxygen content used for detecting fault in a blood oxygen sensor according to claim 5, wherein the blood oxygen sensor interface is a connector configured to couple with the blood oxygen sensor.

9. A method for detecting a fault condition in a blood oxygen sensor configured to measure blood oxygen content using a photodiode, comprising:

receiving current signals from the photodiode, the current signals measured at a pair of terminals;

converting the current signals into terminal voltage signals;

generating a group of comparison voltages V1 and V2 using the terminal voltage signals; and detecting a fault condition relating to the photodiode by comparing the group of voltages V1 and V2.

10. The method for detecting a fault condition in a blood oxygen sensor according to claim 9, wherein detecting the fault condition relating to the photodiode comprises:

detecting a first fault condition relating to the photodiode if V1=V2=0;

detecting a second fault condition relating to the photodiode if V1 does not equal V2, V1 is non-zero, and V2 is non-zero;

detecting a third fault condition relating to the photodiode if V1 is zero and V2 is non-zero or V2 is zero and V1 is non-zero; and detecting a no-fault condition if V1=V2≠0.

11. The method for detecting a fault condition in a blood oxygen sensor according to claim 10, wherein the blood oxygen sensor comprises a signal transmission line coupled to the photodiode, and wherein the signal transmission line comprises a first core, a second core, a third core, and a forth core, and wherein the first fault condition indicates one of an open-circuit in the first core, an open-circuit in the second core, and the first core in a short-circuit connection with the second core, the second fault condition indicates that the first core or the second core is in a short-circuit connection with the third core or the fourth core, and the third fault condition indicates that the first core is in a short-circuit connection with ground or a shielding line if V1 is zero, and indicates that the second core is in a short-circuit connection with ground or a shielding line if V2 is zero.

* * * * *

UNITED STATES PATENT AND TRADEMARK OFFICE
CERTIFICATE OF CORRECTION

PATENT NO. : 7,650,175 B2
APPLICATION NO. : 11/316189
DATED : January 19, 2010
INVENTOR(S) : Liao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1062 days.

Signed and Sealed this

Twenty-third Day of November, 2010

David J. Kappos
*Director of the United States Patent and Trademark Office*